(12) United States Patent
Kwak et al.

(10) Patent No.: US 8,092,496 B2
(45) Date of Patent: Jan. 10, 2012

(54) METHODS AND DEVICES FOR POSTERIOR STABILIZATION

(75) Inventors: SeungKyu Daniel Kwak, Grafton, MA (US); Amie Borgstrom, North Attleborough, MA (US); John Riley Hawkins, Cumberland, RI (US); William Dunbar, Norton, MA (US)

(73) Assignee: DePuy Spine, Inc., Raynham, MA (US)

( * ) Notice: Subject to any disclaimer, the term of this patent is extended or adjusted under 35 U.S.C. 154(b) by 1244 days.

(21) Appl. No.: 11/160,375

(22) Filed: Jun. 21, 2005

(65) Prior Publication Data

US 2006/0079896 A1 Apr. 13, 2006

Related U.S. Application Data

(63) Continuation-in-part of application No. 10/955,207, filed on Sep. 30, 2004, and a continuation-in-part of application No. 10/905,374, filed on Dec. 30, 2004, and a continuation-in-part of application No. 10/905,376, filed on Dec. 30, 2004, and a continuation-in-part of application No. 10/908,882, filed on May 31, 2005.

(51) Int. Cl.
*A61B 17/70* (2006.01)

(52) U.S. Cl. ........................................... 606/247

(58) Field of Classification Search ............... 606/61
See application file for complete search history.

(56) References Cited

U.S. PATENT DOCUMENTS

| | | | |
|---|---|---|---|
| 3,648,691 A | 3/1972 | Lumb et al. | |
| 3,693,616 A | 9/1972 | Roaf et al. | |
| 4,448,191 A | 5/1984 | Rodnyansky et al. | |
| 4,743,260 A | 5/1988 | Burton | |
| 5,084,049 A | 1/1992 | Asher et al. | |
| 5,092,866 A | 3/1992 | Breard | |
| 5,152,303 A | 10/1992 | Allen | |
| 5,176,680 A | 1/1993 | Vignaud et al. | |
| 5,190,543 A | 3/1993 | Schlapfer | |
| 5,261,911 A | 11/1993 | Carl | |
| 5,282,863 A | 2/1994 | Burton | |
| 5,290,312 A | 3/1994 | Kojimoto et al. | |
| 5,306,275 A | 4/1994 | Bryan | |
| 5,360,429 A | 11/1994 | Jeanson et al. | |
| 5,375,823 A | 12/1994 | Navas et al. | |
| 5,387,213 A | 2/1995 | Breard et al. | |
| 5,403,316 A | 4/1995 | Ashman | |

(Continued)

FOREIGN PATENT DOCUMENTS

EP 0576379 A1 12/1993

(Continued)

OTHER PUBLICATIONS

EP Search Report, Application No. 05849737.1, Aug. 6, 2009.

*Primary Examiner* — Eduardo C Robert
*Assistant Examiner* — Mary Hoffman
(74) *Attorney, Agent, or Firm* — Nutter McClennen & Fish LLP

(57) ABSTRACT

Various methods and devices for replacing damaged, injured, diseased, or otherwise unhealthy posterior elements, such as the facet joints, the lamina, the posterior ligaments, and/or other features of a patient's spinal column, are provided. In certain exemplary embodiments, a four bar linkage mechanism can be used to construct spinal stabilization devices and methods for restoring function to adjacent vertebrae. In particular, spinal stabilization devices can be provided that kinematically form a four-bar linkage mechanism with adjacent vertebrae and a disc or other element disposed between the adjacent vertebrae.

19 Claims, 10 Drawing Sheets

U.S. PATENT DOCUMENTS

| | | | |
|---|---|---|---|
| 5,415,661 A | 5/1995 | Holmes | |
| 5,425,732 A | 6/1995 | Ulrich et al. | |
| 5,437,669 A | 8/1995 | Yuan et al. | |
| 5,437,671 A | 8/1995 | Lozier et al. | |
| 5,474,086 A | 12/1995 | McCormick et al. | |
| 5,486,174 A | 1/1996 | Fournet-Fayard et al. | |
| 5,496,318 A | 3/1996 | Howland et al. | |
| 5,540,688 A | 7/1996 | Navas | |
| 5,556,431 A | 9/1996 | Buttner-Janz | |
| 5,562,737 A * | 10/1996 | Graf | 623/17.14 |
| 5,571,191 A | 11/1996 | Fitz | |
| 5,591,165 A | 1/1997 | Jackson | |
| 5,601,554 A | 2/1997 | Howland et al. | |
| 5,672,175 A | 9/1997 | Martin | |
| 5,681,312 A | 10/1997 | Yuan et al. | |
| 5,716,355 A | 2/1998 | Jackson et al. | |
| 5,725,582 A | 3/1998 | Bevan et al. | |
| 5,733,284 A | 3/1998 | Martin et al. | |
| 5,755,796 A | 5/1998 | Ibo et al. | |
| 5,766,254 A | 6/1998 | Gelbard | |
| 5,810,815 A | 9/1998 | Morales | |
| RE36,221 E | 6/1999 | Breard et al. | |
| 5,928,233 A | 7/1999 | Apfelbaum et al. | |
| 5,938,663 A * | 8/1999 | Petreto | 606/61 |
| 5,961,516 A | 10/1999 | Graf | |
| 6,019,760 A | 2/2000 | Metz-Stavenhagen et al. | |
| RE36,758 E | 6/2000 | Fitz | |
| 6,132,464 A | 10/2000 | Martin | |
| 6,241,730 B1 | 6/2001 | Alby | |
| 6,248,106 B1 | 6/2001 | Ferree | |
| 6,267,764 B1 | 7/2001 | Elberg | |
| 6,273,888 B1 | 8/2001 | Justis | |
| 6,355,038 B1 | 3/2002 | Pisharodi | |
| 6,364,883 B1 | 4/2002 | Santilli | |
| 6,419,703 B1 | 7/2002 | Fallin | |
| 6,440,169 B1 | 8/2002 | Elberg et al. | |
| 6,468,276 B1 | 10/2002 | McKay | |
| 6,547,790 B2 | 4/2003 | Harkey, III et al. | |
| 6,551,322 B1 | 4/2003 | Lieberman | |
| 6,551,332 B1 | 4/2003 | Nguyen et al. | |
| 6,554,831 B1 | 4/2003 | Rivard et al. | |
| 6,554,832 B2 * | 4/2003 | Shluzas | 606/61 |
| 6,565,605 B2 | 5/2003 | Goble | |
| 6,579,319 B2 | 6/2003 | Goble | |
| 6,610,091 B1 | 8/2003 | Reiley | |
| 6,626,904 B1 * | 9/2003 | Jammet et al. | 606/61 |
| 6,626,909 B2 | 9/2003 | Chin | |
| 6,626,944 B1 | 9/2003 | Taylor | |
| 6,645,207 B2 | 11/2003 | Dixon | |
| 6,669,729 B2 | 12/2003 | Chin | |
| 6,811,567 B2 | 11/2004 | Reiley | |
| 7,011,685 B2 | 3/2006 | Arnin et al. | |
| 7,074,237 B2 | 7/2006 | Goble et al. | |
| 7,104,992 B2 | 9/2006 | Bailey | |
| 7,189,236 B2 | 3/2007 | Taylor et al. | |
| 7,270,665 B2 | 9/2007 | Morrison et al. | |
| 7,276,069 B2 | 10/2007 | Biedermann et al. | |
| 7,722,649 B2 | 5/2010 | Biedermann et al. | |
| 7,766,940 B2 | 8/2010 | Kwak et al. | |
| 7,799,054 B2 | 9/2010 | Kwak et al. | |
| 7,896,906 B2 | 3/2011 | Kwak et al. | |
| 2002/0029039 A1 * | 3/2002 | Zucherman et al. | 606/61 |
| 2002/0055740 A1 | 5/2002 | Lieberman | |
| 2002/0065557 A1 | 5/2002 | Goble et al. | |
| 2002/0072800 A1 | 6/2002 | Goble et al. | |
| 2002/0123806 A1 | 9/2002 | Reiley | |
| 2002/0133155 A1 | 9/2002 | Ferree | |
| 2002/0151978 A1 | 10/2002 | Zacouto et al. | |
| 2003/0004572 A1 | 1/2003 | Goble et al. | |
| 2003/0028250 A1 | 2/2003 | Reiley et al. | |
| 2003/0055427 A1 | 3/2003 | Graf | |
| 2003/0083657 A1 | 5/2003 | Drewry | |
| 2003/0093078 A1 | 5/2003 | Ritland | |
| 2003/0109880 A1 | 6/2003 | Shirado et al. | |
| 2003/0135277 A1 | 7/2003 | Bryan et al. | |
| 2003/0153912 A1 | 8/2003 | Graf | |
| 2003/0171749 A1 | 9/2003 | Le Couedic et al. | |
| 2003/0171750 A1 | 9/2003 | Chin | |
| 2003/0176926 A1 | 9/2003 | Boehm et al. | |
| 2003/0187438 A1 | 10/2003 | Assaker et al. | |
| 2003/0187454 A1 | 10/2003 | Gill et al. | |
| 2003/0191470 A1 | 10/2003 | Ritland | |
| 2003/0191532 A1 | 10/2003 | Goble et al. | |
| 2003/0220642 A1 | 11/2003 | Freudiger | |
| 2003/0220643 A1 * | 11/2003 | Ferree | 606/61 |
| 2004/0002708 A1 * | 1/2004 | Ritland | 606/61 |
| 2004/0006391 A1 | 1/2004 | Reiley | |
| 2004/0015174 A1 | 1/2004 | Null et al. | |
| 2004/0049189 A1 | 3/2004 | Le Couedic et al. | |
| 2004/0049190 A1 | 3/2004 | Biedermann et al. | |
| 2004/0049272 A1 | 3/2004 | Reiley | |
| 2004/0049273 A1 | 3/2004 | Reiley | |
| 2004/0049274 A1 | 3/2004 | Reiley | |
| 2004/0049275 A1 | 3/2004 | Reiley | |
| 2004/0049276 A1 | 3/2004 | Reiley | |
| 2004/0049277 A1 | 3/2004 | Reiley | |
| 2004/0049278 A1 | 3/2004 | Reiley | |
| 2004/0049281 A1 | 3/2004 | Reiley | |
| 2004/0073215 A1 | 4/2004 | Carli | |
| 2004/0097950 A1 | 5/2004 | Foley et al. | |
| 2004/0111154 A1 | 6/2004 | Reiley | |
| 2004/0116927 A1 | 6/2004 | Graf | |
| 2004/0127989 A1 | 7/2004 | Dooris et al. | |
| 2004/0133203 A1 * | 7/2004 | Young et al. | 606/61 |
| 2004/0138660 A1 | 7/2004 | Serhan | |
| 2004/0143264 A1 | 7/2004 | McAfee | |
| 2004/0147928 A1 | 7/2004 | Landry et al. | |
| 2004/0186475 A1 | 9/2004 | Falahee | |
| 2004/0186575 A1 | 9/2004 | Varga et al. | |
| 2004/0236329 A1 | 11/2004 | Panjabi | |
| 2004/0249379 A1 | 12/2004 | Winslow et al. | |
| 2004/0267259 A1 | 12/2004 | Mazda et al. | |
| 2005/0033431 A1 | 2/2005 | Gordon et al. | |
| 2005/0033432 A1 | 2/2005 | Gordon et al. | |
| 2005/0033434 A1 | 2/2005 | Berry | |
| 2005/0033439 A1 | 2/2005 | Gordon et al. | |
| 2005/0049076 A1 | 3/2005 | Atkinson et al. | |
| 2005/0055096 A1 * | 3/2005 | Serhan et al. | 623/17.11 |
| 2005/0085815 A1 | 4/2005 | Harms et al. | |
| 2005/0101954 A1 | 5/2005 | Simonson | |
| 2005/0101956 A1 | 5/2005 | Simonson | |
| 2005/0113927 A1 | 5/2005 | Malek | |
| 2005/0119748 A1 | 6/2005 | Reiley et al. | |
| 2005/0131409 A1 | 6/2005 | Chervitz et al. | |
| 2005/0171610 A1 | 8/2005 | Humphreys et al. | |
| 2005/0203518 A1 | 9/2005 | Biedermann et al. | |
| 2005/0228381 A1 | 10/2005 | Kirschman | |
| 2005/0228501 A1 | 10/2005 | Miller et al. | |
| 2005/0240265 A1 | 10/2005 | Kuiper et al. | |
| 2005/0245929 A1 | 11/2005 | Winslow et al. | |
| 2005/0256576 A1 * | 11/2005 | Blatt et al. | 623/17.15 |
| 2005/0277922 A1 | 12/2005 | Trieu et al. | |
| 2005/0277930 A1 | 12/2005 | Parsons | |
| 2006/0036240 A1 | 2/2006 | Colleran et al. | |
| 2006/0052785 A1 * | 3/2006 | Augostino et al. | 606/61 |
| 2006/0079896 A1 | 4/2006 | Kwak et al. | |
| 2006/0084976 A1 | 4/2006 | Borgstrom et al. | |
| 2006/0084982 A1 | 4/2006 | Kim | |
| 2006/0084984 A1 | 4/2006 | Kim | |
| 2006/0084991 A1 | 4/2006 | Borgstrom et al. | |
| 2006/0129239 A1 | 6/2006 | Kwak | |
| 2006/0149229 A1 | 7/2006 | Kwak et al. | |
| 2006/0149230 A1 | 7/2006 | Kwak et al. | |
| 2006/0189983 A1 | 8/2006 | Fallin et al. | |
| 2006/0200130 A1 | 9/2006 | Hawkins et al. | |
| 2006/0241771 A1 | 10/2006 | Gordon et al. | |
| 2006/0265074 A1 | 11/2006 | Krishna et al. | |
| 2006/0271046 A1 | 11/2006 | Kwak et al. | |
| 2010/0312283 A1 | 12/2010 | Kwak et al. | |
| 2011/0118787 A1 | 5/2011 | Kwak et al. | |

FOREIGN PATENT DOCUMENTS

| | | |
|---|---|---|
| EP | 0669109 | 2/1994 |
| EP | 0612507 A1 | 8/1994 |
| EP | 669109 A1 | 8/1995 |
| EP | 1153577 | 11/2001 |
| FR | 2694182 A1 | 2/1994 |

| | | | |
|---|---|---|---|
| FR | 2697428 A1 | 5/1994 |
| FR | 2701833 A1 | 9/1994 |
| WO | 0145576 A1 | 6/2001 |
| WO | WO-01/45576 | 6/2001 |
| WO | 0217803 A2 | 3/2002 |
| WO | WO-02/17803 | 3/2002 |
| WO | 0243603 A1 | 6/2002 |
| WO | WO-02/43603 | 6/2002 |
| WO | 02102259 A2 | 12/2002 |
| WO | WO-02/102259 | 12/2002 |

| | | |
|---|---|---|
| WO | 03007828 A1 | 1/2003 |
| WO | WO-03/007828 | 1/2003 |
| WO | 03009737 A1 | 2/2003 |
| WO | WO-03/009737 | 2/2003 |
| WO | 2004024011 A1 | 3/2004 |
| WO | WO-2004/024011 | 3/2004 |
| WO | 2004034916 A1 | 4/2004 |
| WO | WO-2004/034916 | 4/2004 |

* cited by examiner

METHODS AND DEVICES FOR POSTERIOR STABILIZATION

CROSS REFERENCE TO RELATED APPLICATIONS

This application is a continuation-in-part of U.S. patent application Ser. No. 10/955,207, filed on Sep. 30, 2004 and entitled "Posterior Stabilization Systems and Methods," U.S. patent application Ser. No. 10/905,374, filed on Dec. 30, 2004 and entitled "Artificial Facet Joints," U.S. patent application Ser. No. 10/905,376, filed on Dec. 30, 2004 and entitled "Posterior Stabilization System," and U.S. patent application Ser. No. 10/908,882, filed May 31, 2005 and entitled "Facet Joint Replacement." These references are hereby incorporated by reference in their entirety.

BACKGROUND OF THE INVENTION

The vertebrae in a patient's spinal column are linked to one another by the disc and the facet joints, which control movement of the vertebrae relative to one another. Each vertebra has a pair of articulating surfaces located on the left side, and a pair of articulating surfaces located on the right side, and each pair includes a superior articular surface, which faces upward, and an inferior articular surface, which faces downward. Together the superior and inferior articular surfaces of adjacent vertebra form a facet joint. Facet joints are synovial joints, which means that each joint is surrounded by a capsule of connective tissue and produces a fluid to nourish and lubricate the joint. The joint surfaces are coated with cartilage allowing the joints to move or articulate relative to one another.

Diseased, degenerated, impaired, or otherwise painful facet joints and/or discs can require surgery to restore function to the three joint complex. Subsequent surgery may also be required after a laminectomy, as a laminectomy predisposes the patient to instability and may lead to post-laminectomy kyphosis (abnormal forward curvature of the spine), pain, and neurological dysfunction. Damaged, diseased levels in the spine were traditionally fused to one another. While such a technique may relieve pain, it effectively prevents motion between at least two vertebrae. As a result, additional stress may be applied to the adjoining levels, thereby potentially leading to further damage.

More recently, techniques have been developed to restore normal function to the facet joints. One such technique involves covering the facet joint with a cap to preserve the bony and articular structure. Capping techniques, however, are limited in use as they will not remove the source of the pain in osteoarthritic joints. Caps are also disadvantageous as they must be available in a variety of sizes and shapes to accommodate the wide variability in the anatomical morphology of the facets. Caps also have a tendency to loosen over time, potentially resulting in additional damage to the joint and/or the bone support structure containing the cap.

Other techniques for restoring the normal function to the posterior element involve arch replacement, in which superior and inferior prosthetic arches are implanted to extend across the vertebra. The arches may have rigid surfaces that can articulate relative to one another to replace the articulating function of the facet joints. However, aligning two articulating rigid surfaces for facet replacements can be very difficult given the variations in patient anatomy and various motion required (i.e., flexion, extension, lateral bending, and translations).

Accordingly, there remains a need for improved systems and methods for stabilizing adjacent vertebrae and more preferably for restoring normal function to adjacent vertebrae.

FIELD OF THE INVENTION

The present invention relates to methods and devices for stabilizing posterior elements of the spinal column.

BRIEF SUMMARY OF THE INVENTION

The present invention provides methods and devices for stabilizing adjacent vertebrae, and in particular exemplary methods and devices that utilize a four bar linkage concept are provided for restoring function to adjacent vertebrae. In one exemplary embodiment, an implant for stabilizing adjacent vertebrae is provided and it includes a body that is adapted to couple to first and second adjacent vertebrae and that is adapted to move relative to the adjacent vertebrae such that the body kinematically forms a four bar linkage mechanism in the sagittal plane with the adjacent vertebrae and a disc disposed between the adjacent vertebrae.

The body can have a variety of configurations to kinematically form a four bar linkage with the adjacent vertebrae and the disc between the vertebrae, but in one exemplary embodiment the body can include two joints that are adapted to allow movement of the body relative to adjacent vertebrae. The joints can be, for example, two sliding joints, or one sliding joint and one rotating joint. One exemplary sliding joint includes, by way of non-limiting example, a sleeve that is adapted to slidably receive a rod. One exemplary rotating joint includes, by way of non-limiting example, a ball that is adapted to be rotatably disposed within a socket. In use, the joints can allow flexion and extension of adjacent vertebrae.

In another embodiment, an implant for stabilizing adjacent vertebrae is provided and includes a rigid body having a first joint for movably coupling to a first vertebra and a second joint for movably coupling to a second adjacent vertebra. The first and second joints are each adapted to provide one degree of freedom in a sagittal plane when coupled to adjacent vertebrae such that the rigid body is adapted to restore function to adjacent vertebrae coupled thereto in combination with a disc disposed between the adjacent vertebrae. While the configuration of the joints can vary, in one embodiment a center of rotation of each of the first and second joints can be positioned substantially horizontal relative to one another. In another embodiment, at least one of the first and second joints can be adapted to slide vertically when the first and second joints are coupled to adjacent vertebrae.

In yet another exemplary embodiment, an implant is provided for stabilizing adjacent vertebrae in a patient's spine and the implant includes a first linkage that is adapted to rigidly couple to a first vertebra, a second linkage that is adapted to rigidly couple to a second adjacent vertebra, and a body for movably connecting the first and second linkages. When implanted, the first and second linkages and the body are adapted to kinematically form a four bar linkage mechanism in the sagittal plane with a disc disposed between the adjacent vertebrae to restore function to the adjacent vertebrae.

The body can have a variety of configurations, but in one embodiment the body can include first and second joints that are adapted to allow movement of the body relative to the first and second linkages. The first and second joints can each be adapted to slidably move relative to the first and second linkages, or alternatively one of the first and second joints can be adapted to slidably move relative to one of the first and second linkages, and the other one of the first and second joints can be adapted to rotatably move relative to the other one of the first and second linkages. Sliding movement can be achieved using, for example, a sleeve that is adapted to slidably receive a rod formed on the first and second linkages, and rotating movement can be achieved using, for example, a ball that is adapted to be rotatably disposed within a socket formed on one of the first and second linkages. The sleeve can, in certain exemplary embodiments, be formed in the ball.

In other aspects, a method for restoring function to adjacent superior and inferior vertebrae is provided and includes coupling adjacent superior and inferior vertebrae with a moving linkage to kinematically form a four bar linkage mechanism in the sagittal plane with the adjacent superior and inferior vertebrae and a disc disposed between the adjacent superior and inferior vertebrae, thereby restoring function to the adjacent superior and inferior vertebrae. The disc can be a natural disc or it can be an artificial disc that is adapted to allow movement between the adjacent superior and inferior vertebrae. Where an artificial disc is used, the method can include the step of implanting the artificial disc between the adjacent superior and inferior vertebrae.

Various techniques can be used to couple adjacent superior and inferior vertebrae with a moving linkage, but in one embodiment a first member can be rigidly mated to a superior vertebra, a second member can be rigidly mated to an inferior vertebra, and the moving linkage can be movably coupled to the first and second members. The moving linkage can be adapted to slide relative to both of the first and second members, or alternatively it can be adapted to slide relative to one of the first and second members and to pivot relative to the other one of the first and second members.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
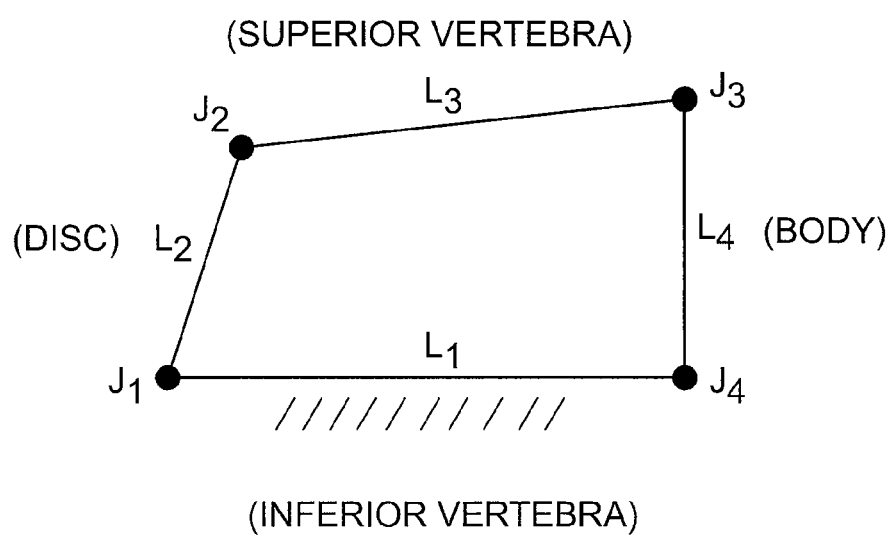
FIG. 1 is a diagram illustration a four bar linkage mechanism for use in constructing a spinal stabilization device to restore function to adjacent vertebrae in a patient's spinal column.

The present invention provides various methods and devices for replacing damaged, injured, diseased, or otherwise unhealthy posterior elements, such as the facet joints, the lamina, the posterior ligaments, and/or other features of a patient's spinal column. In certain exemplary embodiments, a four bar linkage mechanism can be used to construct spinal stabilization devices and methods for restoring function to adjacent vertebrae. A four bar linkage mechanism is a mechanism that lies in a plane and that consists of four linkages that are connected by four joints that allow movement in the plane of the mechanism. Typically, one of the linkages is fixed so that it does not move. As applied to the spinal column, a spinal stabilization device can be constructed to dynamically form a four bar linkage mechanism, when movement is viewed in the sagittal plane, with the adjacent vertebrae and a disc (or some other element) disposed between the adjacent vertebrae. In particular, with reference to FIG. 1, one of the vertebrae, e.g., an inferior vertebra, can form a first, fixed linkage $L_1$. Since the disc moves relative to the inferior vertebra, the disc can form a second linkage $L_2$ that is coupled to the first linkage $L_1$ (inferior vertebra). Movement between the second linkage $L_2$ (disc) and the first linkage $L_1$ (inferior vertebra) can be represented as a first joint $J_1$. The disc can also move relative to an adjacent superior vertebra, and thus the superior vertebra can form a third linkage $L_3$. Movement between the third linkage $L_3$ (superior vertebra) and the second linkage $L_2$ (disc) can be represented as a second joint $J_2$. The superior vertebra can, in turn, be movably coupled to the inferior vertebra by a body, which can form a fourth linkage $L_4$. Movement between the fourth linkage $L_4$ (body) and the third linkage $L_3$ (superior vertebra) can be represented as a third joint $J_3$, and movement between the fourth linkage $L_4$ (body) and the first linkage $L_1$ (inferior vertebra) can be represented as a fourth joint $J_4$. Accordingly, the inferior vertebra, the disc, the superior vertebra, and a body together can kinematically form a four bar linkage mechanism in the sagittal plane. A person skilled in the art will appreciate that, while FIG. 1 illustrates a substantially rectangular four bar linkage mechanism, the length and angular orientation of the linkages $L_1$-$L_4$ can vary. A person skilled in the art will also appreciate that the spinal stabilization device can be disposed on any posterior portion of the spinal column, and that the structure of the device is not limited to be positioned in the sagittal plane. The four bar linkage mechanism is merely used to explain the resulting movement that occurs when the device is viewed in the sagittal plane.

This four bar linkage mechanism can be used to construct a variety of spinal stabilization devices and methods for restoring function to adjacent vertebrae. For example, while the body that forms the fourth linkage $L_4$ is preferably rigid, at least in the sagittal plane, the body can have a variety of shapes, sizes, and orientations, and it can be coupled to the adjacent vertebrae using a variety of joints $J_3$, $J_4$. The joints $J_3$, $J_4$ can be, for example, joints that pivot in the sagittal plane, joints that slide in the sagittal plane, or combinations thereof. The disc that forms the second linkage $L_2$, as well as the joints $J_1$, $J_2$ that allow movement of the disc relative to the adjacent vertebrae, can also have a variety of configurations. For example, the disc can be a natural disc, an artificial disc, or any other element that is disposed between the adjacent vertebrae and that allows at least two degrees of freedom when implanted between adjacent vertebrae. The joints $J_1$, $J_2$ that allow movement of the disc can also be sliding and/or pivoting joints. Accordingly, a person skilled in the art will appreciate that a variety of techniques can be used to provide spinal stabilization devices that kinematically form a four bar linkage mechanism in the sagittal plane. A person skilled in the art will also understand that the various exemplary stabilization devices described and shown herein are merely relied on for illustration purposes to demonstrate various constructs that kinematically form a four bar linkage mechanism in the sagittal plane when implanted.

At the outset, it is important to note that since a natural disc has three degrees of freedom when viewed in the sagittal plane, it normally could not be considered to dynamically form one of the rigid linkages of a four bar linkage mechanism. Regardless, a person skilled in the art will appreciate that the methods and devices disclosed herein are not intended to be limited to use with spinal discs having only two degrees of freedom, even though conceptually a disc have two degrees of freedom in the sagittal plane is necessary to form a four bar linkage concept. The methods and devices will function properly with a natural disc, and thus any reference herein to a disc that forms a linkage of a four bar linkage mechanism in the sagittal plane is intended to include a natural disc, i.e., a disc have two or more degrees of freedom.

Figure 2A:
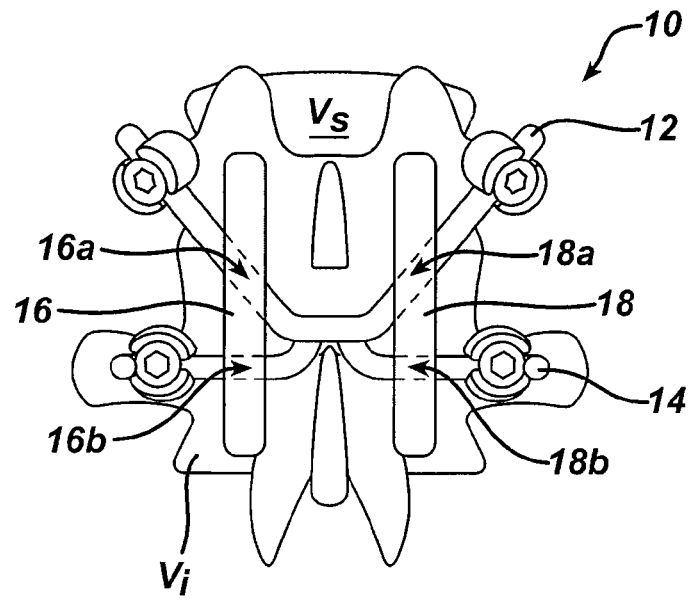
FIG. 2A is a posterior view of one embodiment of a spinal stabilization device coupled to adjacent superior and inferior vertebrae.
Figure 2B:
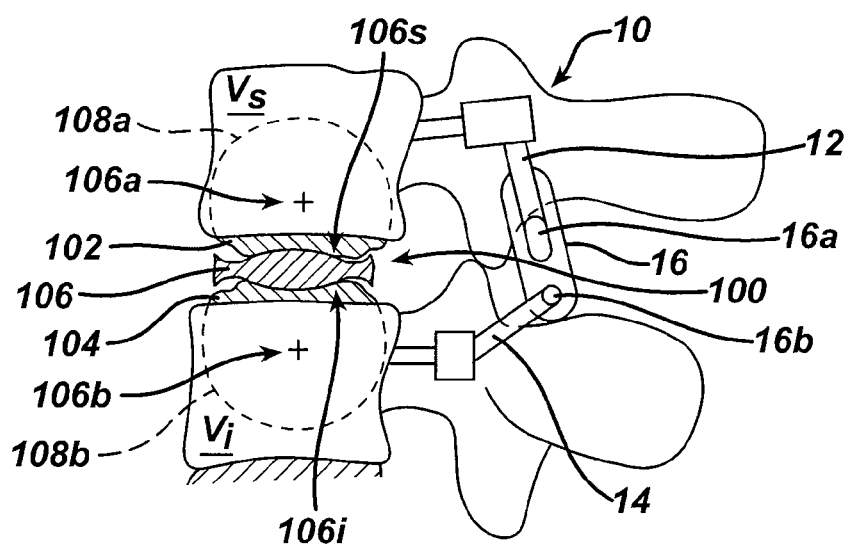
FIG. 2B is a side view of the spinal stabilization device shown in FIG. 2A.

FIGS. 2A and 2B illustrate one exemplary embodiment of a spinal stabilization device 10 that kinematically forms a four bar linkage mechanism in the sagittal plane when connected between adjacent vertebrae Vs, Vi. As shown, the device 10 generally includes a first connecting element 12 that is adapted to rigidly couple to a first vertebra, e.g., a superior vertebra Vs, and a second connecting element 14 that is adapted to rigidly couple to a second adjacent vertebra, e.g., an inferior vertebra Vi. A variety of techniques can be used to attach the connectors 12, 14 to the adjacent vertebrae Vs, Vi, but in the illustrated embodiment the connectors 12, 14 are mated to the vertebrae Vs, Vi using bone screws to form a rigid connection. The device 10 also includes first and second bodies 16, 18 that are adapted to movably couple to the first and second connectors 12, 14 to allow movement of the adjacent vertebrae Vs, Vi. While various techniques can be used to movably couple each body 16, 18 to the connectors 12, 14, in the illustrated exemplary embodiment each body 16, 18 includes a first bore 16a, 18a formed therein and adapted to receive the first connector 12, and a second bore 16b, 18b formed therein and adapted to receive the second connector 14. The first bore 16a, 18a in each body 16, 18 allows the first connector 12 to slide relative to the bodies 16, 18 thereby allowing flexion of the adjacent vertebrae Vs, Vi coupled thereto. The bodies 16, 18 can also optionally be flexible to allow additional flexion and/or to control movement of the adjacent vertebrae. The spinal stabilization device 10 and other exemplary embodiments of spinal stabilization devices are described in more detail in U.S. patent application Ser. No. 10/955,207, filed on Sep. 30, 2004 and entitled "Posterior Stabilization Systems and Methods."

FIG. 2B illustrates the device 10 in the sagittal plane, showing one of the bodies, e.g., body 16 movably coupled to the first and second connectors 12, 14, which in turn are coupled to the adjacent vertebrae Vs, Vi. As is further shown, an artificial disc 100 is implanted between the adjacent vertebrae Vs, Vi. In general, the illustrated disc 100 includes a superior endplate member 102 that rigidly connects to the superior vertebra Vs, an inferior endplate member 104 that rigidly connects to the inferior vertebra Vi, and a core 106 movably disposed therebetween. The core 106 has convex superior and inferior surfaces 106s, 106i that sit within corresponding concave surfaces formed in the superior and inferior endplate members 102, 104, thereby allowing the core 106 to pivot with respect to the endplate members 102, 104. As previously noted, the spinal stabilization implants disclosed herein can be used with an artificial disc have virtually any configuration, or with a natural disc or any other element that allows movement between adjacent vertebrae Vs, Vi. In an exemplary embodiment, however, the disc is preferably adapted to provide at least two degrees of freedom when implanted between adjacent vertebrae. By way of non-limiting example, one exemplary artificial disc for use with the present invention is the Charité™ Artificial Disc available from DePuy Spine, Inc.

Figure 2C:
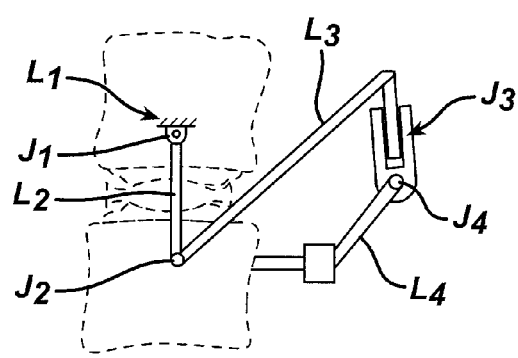
FIG. 2C is a side view showing the spinal stabilization device of FIG. 2B kinematically reduced to a form a four bar linkage mechanism in the sagittal plane.

In use, referring to FIGS. 2B and 2C, the device 10 can kinematically form a four bar linkage mechanism in the sagittal plane to control movement of the adjacent vertebrae Vs, Vi. In particular, assuming one of the vertebrae Vs, Vi, e.g., the inferior vertebra Vi, is fixed, the fixed vertebra Vi can represent the first linkage $L_1$ of a four bar linkage mechanism. The core 106 forms the second linkage $L_2$, as the core 106 moves relative to the inferior vertebra Vi. Movement between the core 106 and the inferior vertebra Vi can be represented by a first joint $J_1$. The first joint $J_1$ is located at a center of rotation 106a of a path of movement of the core 106 relative to the inferior vertebra Vi. As shown in FIG. 2B, the inferior surface 106i of the core 106 moves relative to the fixed inferior vertebra Vi along circular path 108a, and thus the center of rotation 106a of the circular path 108a forms the first joint $J_1$ between the core 106, i.e., the second linkage $L_2$, and the inferior vertebra Vi, i.e., the first linkage $L_1$. The first joint $J_1$ is represented in FIG. 2C as a pivot joint since the core 106 pivots relative to the inferior vertebra Vi in the sagittal plane.

Since the core 106 forms the second linkage $L_2$, the superior vertebra Vs forms the third linkage $L_3$, as the superior vertebra Vs moves relative to the core 106. The joint that allows movement between the core 106, i.e., the second linkage $L_2$, and the superior vertebra Vs, i.e., the third linkage $L_3$, is determined by a center of rotation of a path of movement of the core 106 relative to the superior vertebra Vs. As shown in FIG. 2B, the superior surface 106s of the core 106 moves relative to the superior vertebra Vs along a circular path 108b, and thus the center of rotation 106b of the circular path 108b forms the second joint $J_2$ between the core 106, i.e., the second linkage $L_2$, and the superior vertebra Vs, i.e., the third linkage $L_3$. The second joint $J_2$ is represented in FIG. 2C as a pivot joint since the core 106 pivots relative to the superior vertebra Vs in the sagittal plane.

Figure 2D:
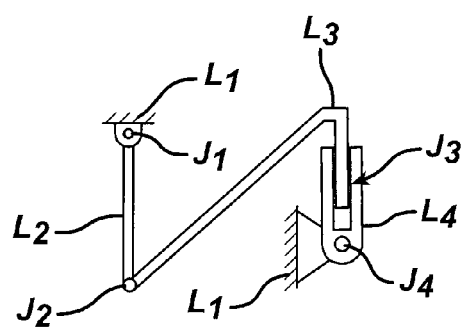
FIG. 2D is a diagram illustrating the four bar linkage mechanism shown in FIG. 2C.
Figure 2E:
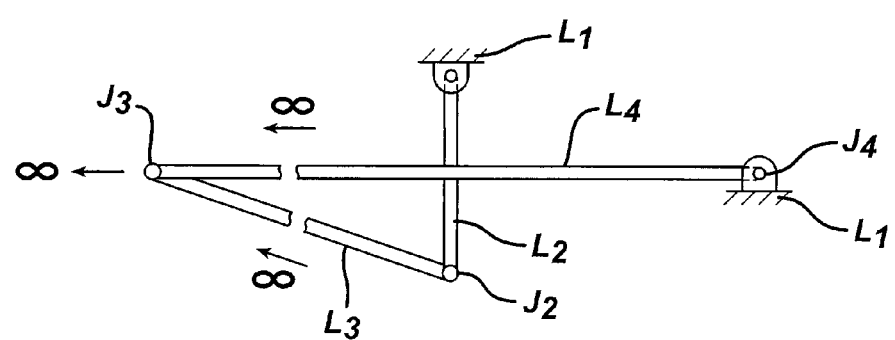
FIG. 2E is a diagram illustrating the four bar linkage mechanism shown in FIG. 2D, showing an infinite linkage.

As is further shown in FIGS. 2B and 2C, the body 16 forms the fourth linkage $L_4$, as the body 16 moves relative to the superior vertebra Vs and the inferior vertebra Vi. The joint that allows movement between the superior vertebra Vs, i.e., the third linkage $L_3$, and the body 16, i.e., the fourth linkage $L_4$, is again determined by the center of rotation of a path of movement of the body 16 relative to the superior vertebra Vs. As shown in FIG. 2B, the body 16 slides in a superior-inferior direction along a straight path. Accordingly, the third joint $J_3$ that couples the body 16, i.e., the fourth linkage $L_4$, to the superior vertebra, i.e., the third linkage $L_3$, is represented as a sliding joint, shown in FIG. 2C, since the body 16 slides in the sagittal plane relative to the superior vertebra Vs. The center of rotation of the path of movement of a straight line is infinite, and thus the third joint $J_3$ that allows movement between the third and fourth linkages $L_3$, $L_4$ is positioned an infinite distance away along the horizontally-extending line that is perpendicular to the sliding joint. In other words, the third and fourth linkages $L_3$, $L_4$ that are coupled by the third joint $J_3$ can each have an infinite length, as shown in FIG. 2E.

Continuing to refer to FIGS. 2B and 2C, the body 16, which forms the third linkage $L_3$, also moves relative to the inferior vertebra Vi, i.e., the first, fixed linkage $L_1$. The fourth joint $J_4$ of the four bar linkage mechanism that allows movement of the body 16 relative to the inferior vertebra Vi is located at a center of rotation of the path of movement of the body 16 relative to the inferior vertebra Vi. As shown in FIG. 2B, the center of rotation is the bore 16b formed in the body 16, as the body 16 pivots about the connector 14 that extends through the bore 16b and that is rigidly coupled to the inferior vertebra Vi. Since the body 16 pivots relatives to the inferior vertebra Vi, the fourth joint $J_4$ is represented as a pivot joint in FIG. 2C. As previously indicated, the device 10 can include two bodies 16, 18, and thus body 18 can provide motion similar to that provided by body 16. In other words, the device 10 can include any number of bodies aligned in the frontal plane to provide movement between the adjacent vertebrae.

In sum, the spinal stabilization device 10 kinematically forms a four bar linkage mechanism in the sagittal plane with adjacent superior and inferior vertebrae Vs, Vi coupled thereto, and with a disc 100 disposed between the adjacent superior and inferior vertebrae Vs, Vi. The four bar linkage mechanism is illustrated in FIGS. 2D and 2E, and it includes four linkages $L_1$-$L_4$ coupled by three pivoting joints $J_1$, $J_2$, and $J_4$ and a sliding joint $J_3$.

Figure 3A:
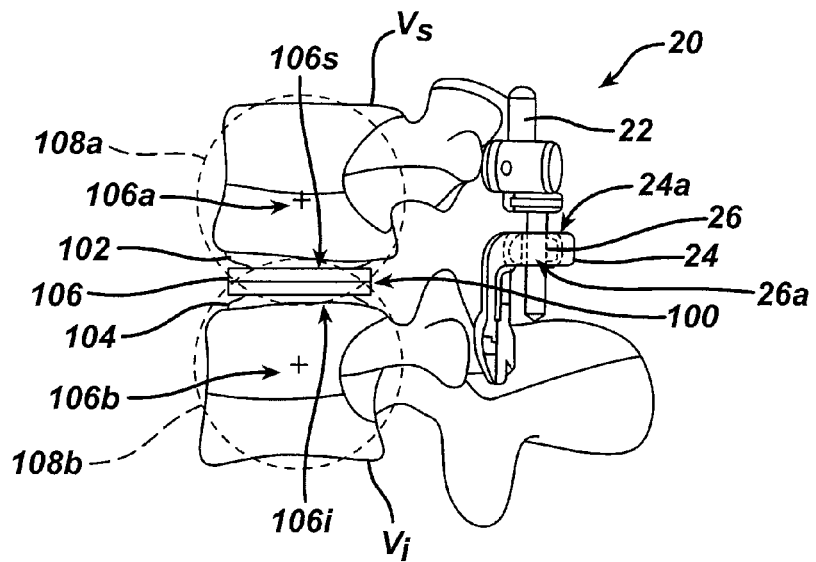
FIG. 3A is a side, partially transparent view of another embodiment of a spinal stabilization device coupled to adjacent superior and inferior vertebrae.

FIG. 3A illustrates another exemplary embodiment of a spinal stabilization device 20 that kinematically forms a four bar linkage mechanism in the sagittal plane when connected between adjacent vertebrae Vs, Vi. As shown, the device 20 generally includes a first connecting element 22 that is adapted to rigidly couple to a first vertebra, e.g., a superior vertebra Vs, and a second connecting element 24 that is adapted to rigidly couple to a second adjacent vertebra, e.g., an inferior vertebra Vi. The first and second connecting elements 22, 24 can each have a variety of shapes and sizes, but in the illustrated embodiment the first connecting element 22 is in the form of an extension rod having a first portion that is adapted to rigidly mate to the superior vertebra Vs, and a second portion that is adapted to slidably couple to a body 26, and the second connecting element 24 is in the form of an L-shaped member having a first portion that is adapted to rigidly mate to the inferior vertebra Vi, and a second portion that is adapted to pivotally couple to a body 26. A variety of techniques can be used to attach the connectors 22, 24 to the adjacent vertebrae Vs, Vi, but in the illustrated embodiment the connectors 22, 24 are mated to the vertebrae Vs, Vi using bone screws to form a rigid connection.

The device 20 also includes a body 26 that is adapted to movably couple to the first and second connectors 22, 24 to allow movement of the adjacent vertebrae Vs, Vi. While various techniques can be used to movably couple the body 26 to the connectors 22, 24, in the illustrated exemplary embodiment the body 26 is in the form of a ball bearing that is rotatably disposed within a socket 24a formed in the second connector 24, and that has a bore 26a formed therethrough for slidably receiving the first connector 22. In use, the sliding joint allows the first connector 22 to slide relative to the body 26, and the ball and socket joint allows the body 26 to pivot relative to the second connector 24, thereby allowing flexion of the adjacent vertebrae Vs, Vi coupled thereto. The spinal stabilization device 20 and other exemplary embodiments of spinal stabilization devices are described in more detail in U.S. patent application Ser. No. 10/905,374, filed on Dec. 30, 2004 and entitled "Artificial Facet Joints," and in U.S. patent application Ser. No. 10/908,882, filed May 31, 2005 and entitled "Facet Joint Replacement."

As is further shown in FIG. 3A, the spinal stabilization device 20 can also be used with artificial disc 100, previously described with respect to FIG. 2A. A person skilled in the art will appreciate that, while artificial disc 100 is shown, the spinal stabilization implants disclosed herein can be used with an artificial disc have virtually any configuration, or with a natural disc or any other element that allows movement between adjacent vertebrae Vs, Vi. However, as previously discussed, the disc is preferably adapted to provide at least two degrees of freedom when implanted between adjacent vertebrae.

Figure 3B:
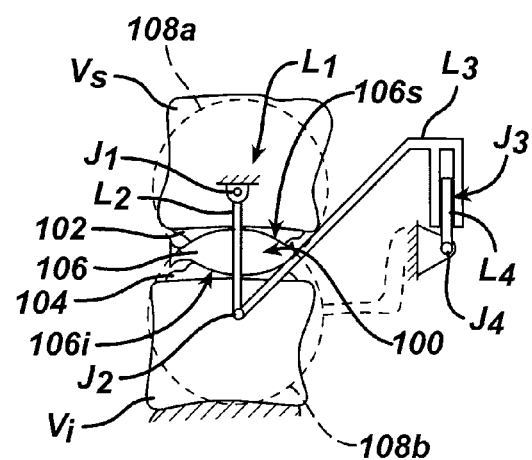
FIG. 3B is a side view showing the spinal stabilization device of FIG. 3A kinematically reduced to a form a four bar linkage mechanism in the sagittal plane.

In use, referring to FIG. 3B, the device 20 can kinematically form a four bar linkage mechanism in the sagittal plane to control movement of the adjacent vertebrae Vs, Vi. As previously explained with respect to FIGS. 2B and 2C, assuming the inferior vertebra Vi is fixed and represents the first linkage $L_1$ of a four bar linkage mechanism, the core 106 of the disc 100 forms the second linkage $L_2$ that is coupled to the inferior vertebra Vi by a first joint $J_1$, which is located at the center of rotation 106a of a circular path of movement 108a of the inferior surface 106i of the core 106. Likewise, as previously explained, the superior vertebra Vs forms the third linkage $L_3$ that is movably coupled to the second linkage $L_2$, e.g., core 106, by a second joint $J_2$, which is located at the center of rotation 106b of a circular path of movement 108b of the superior surface 106s of the core 106. The first and second joints $J_1$, $J_2$ are each represented in FIG. 3B as pivot joints since the core 106 pivots relative to the superior and inferior vertebrae Vs, Vi in the sagittal plane.

As is further shown in FIGS. 3A and 3B, the body 26 forms the fourth linkage $L_4$, as the body 26 moves relative to the superior vertebra Vs and the inferior vertebra Vi. The joint that allows movement between the superior vertebra Vs, i.e., the third linkage $L_3$, and the body 26, i.e., the fourth linkage $L_4$, is again determined by the center of rotation of a path of movement of the body 26 relative to the superior vertebra Vs. As shown in FIG. 3A, the body 26 is slidably movable relative to the first connector 22, which is rigidly coupled to the superior vertebra Vs, and the path of movement of the body 26 extends in a superior-inferior direction along a straight path. Accordingly, the third joint $J_3$ that couples the body 26, i.e., the fourth linkage $L_4$, to the superior vertebra, i.e., the third linkage $L_3$, is represented as a sliding joint, shown in FIG. 3B, since the body 26 slides in the sagittal plane relative to the superior vertebra Vs. As previously explained, the center of rotation of the path of movement of a straight line is infinite, and thus the third joint $J_3$ that allows movement between the third and fourth linkages $L_3$, $L_4$ is positioned an infinite distance away along the horizontally-extending line that is perpendicular to the sliding joint. In other words, the third and fourth linkages $L_3$, $L_4$ that are coupled by the third joint $J_3$ can each have an infinite length, as previously shown in FIG. 2E.

Continuing to refer to FIGS. 3A and 3B, the body 26, which forms the third linkage $L_3$, also moves relative to the inferior vertebra Vi, i.e., the first, fixed linkage $L_1$. In particular, the body 26 pivots relative to the second connector 26 that is rigidly attached to the inferior vertebra Vi. The fourth joint $J_4$ of the four bar linkage mechanism that allows movement of the body 26 relative to the inferior vertebra Vi is therefore a pivoting joint that is located at a center of rotation of the path of movement of the body 26 relative to the inferior vertebra Vi. In the illustrated embodiment, the center of rotation is the bore 26a formed in the body second connector 26, as the body 26 pivots within the bore 26a.

Figure 3C:
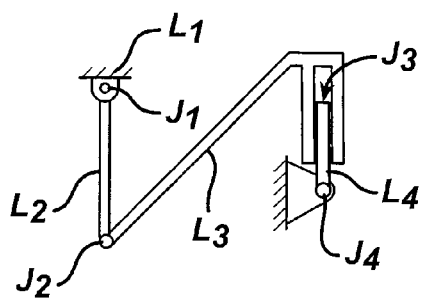
FIG. 3C is a diagram illustrating the four bar linkage mechanism shown in FIG. 3B.

In sum, the spinal stabilization device 20 kinematically forms a four bar linkage mechanism in the sagittal plane with adjacent superior and inferior vertebrae Vs, Vi coupled thereto, and with a disc 100 disposed between the adjacent superior and inferior vertebrae Vs, Vi. The four bar linkage mechanism is illustrated in FIG. 3C, and it includes four linkages $L_1$-$L_4$ coupled by three pivoting joints $J_1$, $J_2$, and $J_4$ and a sliding joint $J_3$.

Figure 4A:
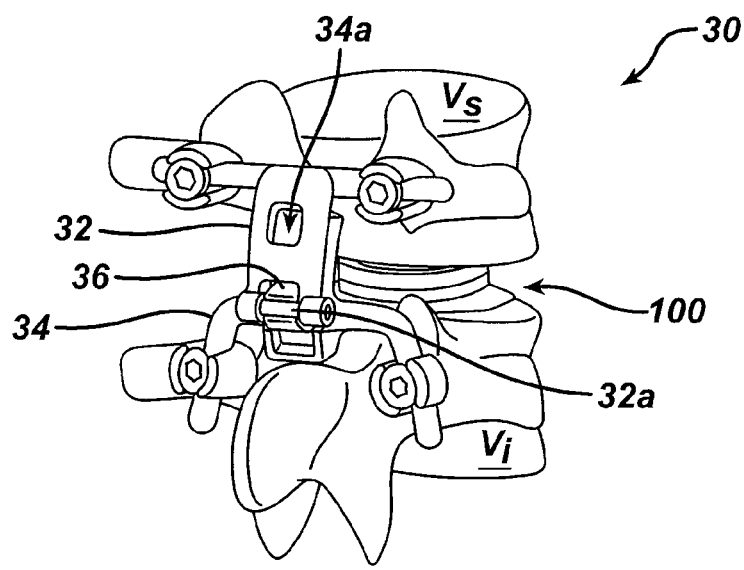
FIG. 4A is a posterior view of yet another embodiment of a spinal stabilization device coupled to adjacent superior and inferior vertebrae.
Figure 4B:
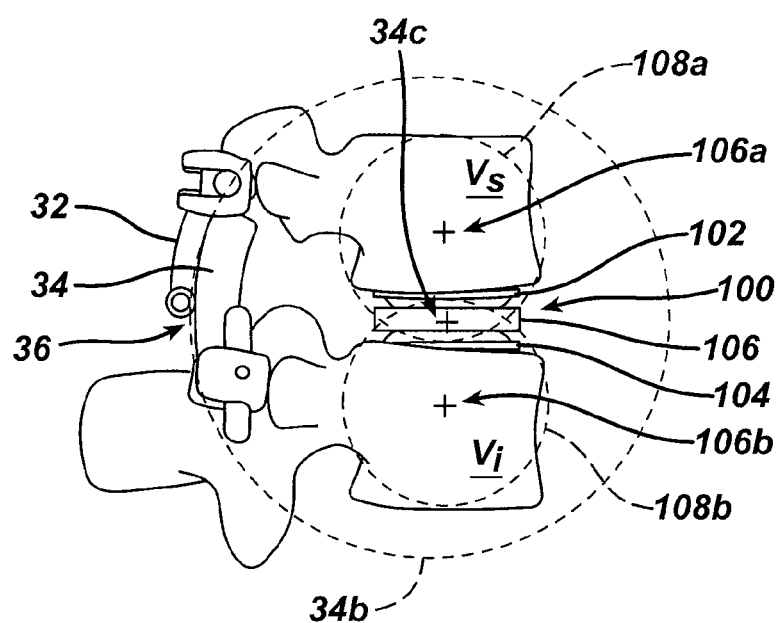
FIG. 4B is a side view of the spinal stabilization device shown in FIG. 4A.

FIGS. 4A and 4B illustrate another exemplary embodiment of a spinal stabilization device 30 that kinematically forms a four bar linkage mechanism in the sagittal plane when connected between adjacent vertebrae Vs, Vi. As shown, the device 30 generally includes a first connecting element 32 that is adapted to rigidly couple to a first vertebra, e.g., a superior vertebra Vs, and a second connecting element 34 that is adapted to rigidly couple to a second adjacent vertebra, e.g., an inferior vertebra Vi. The first and second connecting elements 32, 34 can each have a variety of shapes and sizes, but in the illustrated embodiments the first and second connecting elements 32, 34 each have an elongate central portion that is adapted to couple to a body 36, and opposed arms extending from the elongate central portion for mating to the vertebrae Vs, Vi. A variety of techniques can be used to attach the connectors 32, 34 to the adjacent vertebrae Vs, Vi, but in the illustrated embodiment the connectors 32, 34 are mated to the vertebrae Vs, Vi using bone screws to form a rigid connection.

The device 30 also includes a body 36 that is adapted to movably couple to the first and second connectors 32, 34 to allow movement of the adjacent vertebrae Vs, Vi. While various techniques can be used to movably couple the body 36 to the connectors 32, 34, in the illustrated exemplary embodiment the body 36 is in the form of a triangular member that rotatably mates to a bar 32a formed on the first connecting element 32, and that slides within a pathway 34a formed in the second connecting element 34. As a result of the sliding and pivoting joints, the body 36 allows the first and second connectors 32, 34 to move relative to one another, thereby allowing flexion of the adjacent vertebrae Vs, Vi coupled thereto. The spinal stabilization device 30 and other exemplary embodiments of spinal stabilization devices are described in more detail in U.S. patent application Ser. No. 10/905,376, filed on Dec. 30, 2004 and entitled "Posterior Stabilization System."

As is further shown in FIGS. 4A and 4B, the spinal stabilization device 30 can also be used with artificial disc 100, previously described with respect to FIG. 2A. A person skilled in the art will appreciate that, while artificial disc 100 is shown, the spinal stabilization implants disclosed herein can be used with an artificial disc have virtually any configuration, or with a natural disc or any other element that allows movement between adjacent vertebrae Vs, Vi. Again, in an exemplary embodiment, the disc is preferably adapted to provide at least two degrees of freedom when implanted between adjacent vertebrae.

Figure 4C:
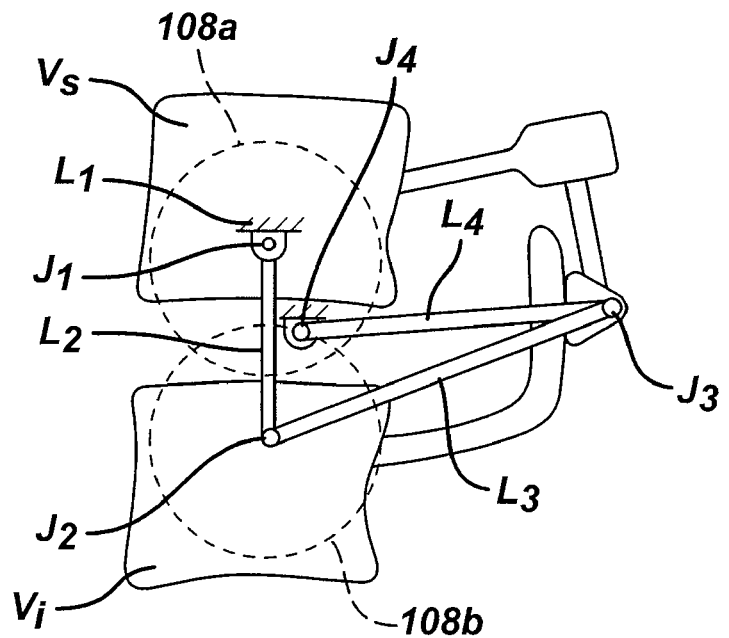
FIG. 4C is a side view showing the spinal stabilization device of FIG. 4B kinematically reduced to a form a four bar linkage mechanism in the sagittal plane.

In use, referring to FIGS. 4B and 4C, the device 30 can kinematically form a four bar linkage mechanism in the sagittal plane to control movement of the adjacent vertebrae Vs, Vi. As previously explained with respect to FIGS. 2B and 2C, assuming the inferior vertebra Vi is fixed and represents the first linkage $L_1$ of a four bar linkage mechanism, the core 106 of the disc 100 forms the second linkage $L_2$ that is coupled to the inferior vertebra Vi by a first joint $J_1$, which is located at the center of rotation 106a of a circular path of movement 108a of the inferior surface 106i of the core 106. Likewise, as previously explained, the superior vertebra Vs forms the third linkage $L_3$ that is movably coupled to the second linkage $L_2$, e.g., core 106, by a second joint $J_2$, which is located at the center of rotation 106b of a circular path of movement 108b of the superior surface 106s of the core 106. The first and second joints $J_1$, $J_2$ are each represented in FIG. 4C as pivot joints since the core 106 pivots relative to the superior and inferior vertebrae Vs, Vi in the sagittal plane.

As is further shown in FIGS. 4B and 4C, the body 36 forms the fourth linkage $L_4$, as the body 36 moves relative to the superior vertebra Vs and the inferior vertebra Vi. The joint that allows movement between the superior vertebra Vs, i.e., the third linkage $L_3$, and the body 36, i.e., the fourth linkage $L_4$, is again determined by the center of rotation of a path of movement of the body 36 relative to the superior vertebra Vs. In this embodiment, as shown in FIG. 4B, the body 36 pivots relative to the first connector 34 that is rigidly attached to the superior vertebra Vs. The third joint $J_3$ of the four bar linkage mechanism that allows movement of the body 36 relative to the superior vertebra Vs is therefore a pivoting joint that is located at a center of rotation of the path of movement of the body 36 relative to the superior vertebra Vi. In the illustrated embodiment, the center of rotation is the bar 32a formed on first connector 32, as the body 36 pivots about the bar 32a.

Continuing to refer to FIGS. 4B and 4C, the body 36, which forms the third linkage $L_3$, also moves relative to the inferior vertebra Vi, i.e., the first, fixed linkage $L_1$. In particular, the body 36 slidably moves along a circular path 34b relative to the second connector 34, which is rigidly coupled to the inferior vertebra Vi. The center of rotation 34c of the circular path 34b thus forms the fourth joint $J_4$ that couples the body 36, i.e., the fourth linkage $L_4$, to the inferior vertebra Vi, i.e., the first linkage $L_1$. The fourth joint $J_4$ is represented as a pivoting joint, shown in FIG. 4C, since the body 36 slidably moves about a circular path in the sagittal plane relative to the inferior vertebra Vi. A person skilled in the art will appreciate that the joints $J_3$ and $J_4$ can be positioned at different locations. For example, although joint $J_4$ currently lies near the center of the disc, the joint $J_4$ can be placed more posteriorly, forming a shorter link $L_4$. The joint $J_4$ could also be placed posterior to joint $J_3$.

Figure 4D:
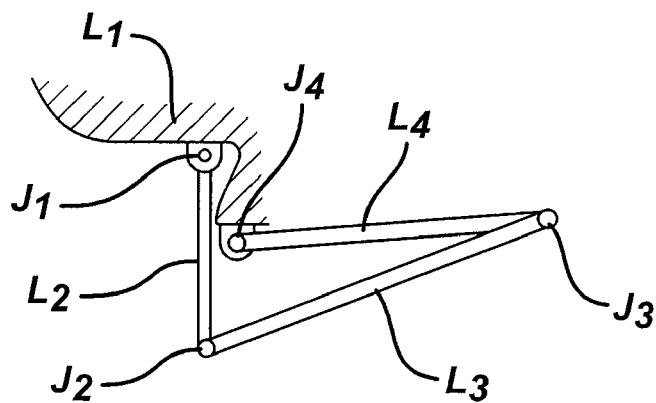
FIG. 4D is a diagram illustrating the four bar linkage mechanism shown in FIG. 4C.

In sum, the spinal stabilization device 30 kinematically forms a four bar linkage mechanism in the sagittal plane with adjacent superior and inferior vertebrae Vs, Vi coupled thereto, and with a disc 100 disposed between the adjacent superior and inferior vertebrae Vs, Vi. The four bar linkage mechanism is illustrated in FIG. 4D, and it includes four linkages $L_1$-$L_4$ coupled by four pivoting joints $J_1$-$J_4$.

Figure 5A:
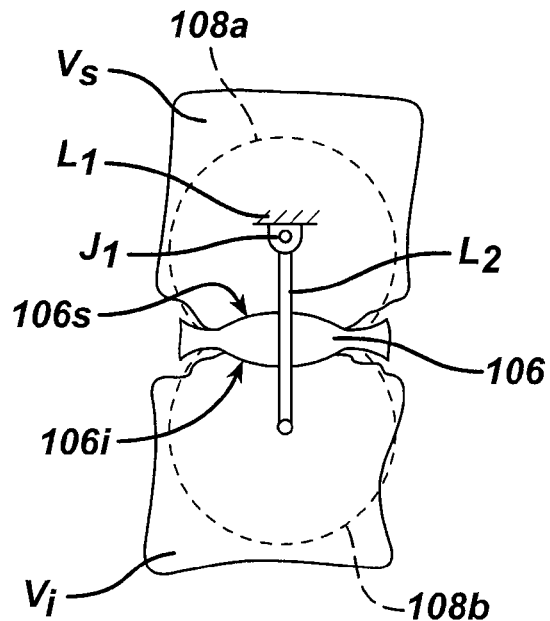
FIG. 5A is a side view of a disc implant disposed between adjacent superior and inferior vertebrae, showing the disc implant kinematically reduced to form a portion of a four bar linkage mechanism in the sagittal plane.
Figure 5B:
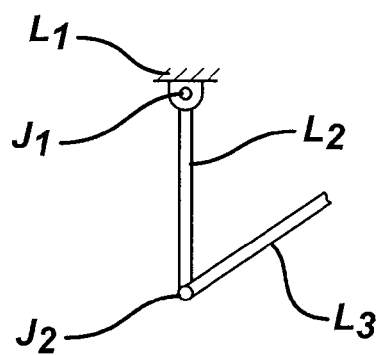
FIG. 5B is a diagram illustrating a portion of the four bar linkage mechanism shown in FIG. 4A.

In each of the various embodiments described above, the spinal stabilization devices 10, 20, 30 each kinematically form a four bar linkage mechanism in the sagittal plane with adjacent superior and inferior vertebrae Vs, Vi and a core 106 disposed between the vertebrae Vs, Vi. As previously noted, the four bar linkage mechanism can be used to construct a variety of other spinal stabilization devices for restoring function to adjacent vertebrae. A portion of the four bar linkage mechanism can have a construct as shown in FIGS. 5A and 5B, wherein the inferior vertebra Vi forms the first, fixed linkage $L_1$, the core 106 (or any other disc or element disposed between the vertebrae Vs, Vi) forms the second linkage $L_2$ that is coupled to the first linkage $L_1$ by a first pivot joint $J_1$ located at a center of rotation of the path of movement 108a of the inferior surface 106i of the core 106 relative to the inferior vertebra Vi, and the superior vertebra Vs forms the third linkage $L_3$ that is coupled to the second linkage $L_2$ by a second pivot joint $J_2$ located at a center of rotation of the path of movement 108b of the superior surface 106s of the core 106 relative to the superior vertebra Vs. The remainder of the four bar linkage mechanism can be constructed to provide a fourth linkage $L_4$, e.g., a body, and third and fourth joints $J_3$, $J_4$, each of which can have virtually any configuration. As previously indicated, the joints $J_3$, $J_4$ can be sliding joints such as a sleeve and rod, pivoting joints such as a ball and socket, or some combination thereof. In certain exemplary embodiments, the third and fourth joints $J_3$, $J_4$ are two pivoting joints, or one sliding joint and one pivoting joint. Where a sliding joint is used, the joint can be a straight sliding joint or a curved sliding joint. Where a straight sliding joint is used, sliding movement can occur in a generally vertical direction (i.e., in a superior-inferior direction). Where a curved sliding joint is used, the linkage $L_4$ that connects to the joints $J_3$, $J_4$ extends in generally horizontal direction, as previously described. In other words, the center or rotation of each joint $J_3$, $J_4$, where one joint is a curved sliding joint, is aligned generally horizontally.

By way of non-limiting example, FIGS. 6A-7D illustrate a variety of joint combinations and orientations for forming a spinal stabilization device that kinematically forms a four bar linkage mechanism in the sagittal plane with adjacent vertebrae and a disc disposed therebetween. In FIGS. 6A-6H, each four bar linkage mechanism includes one sliding joint and one pivoting joint. The orientation of each joint is varied to illustrate some possible configurations for forming a spinal stabilization device. For example, in FIG. 6A the four bar linkage mechanism includes a first, fixed linkage $L_1$ (first vertebra), a second linkage $L_2$ (disc) that is pivotally coupled to the first linkage $L_1$ by a first joint $J_1$, a third linkage $L_3$ (second adjacent vertebra) that is pivotally coupled to the second linkage $L_2$, and a fourth linkage $L_4$ (body) that is slidably coupled to the third linkage $L_3$ and that is pivotally coupled to the first linkage $L_1$. In this embodiment, the fourth linkage $L_4$ (body) includes a rod that is slidably disposed through a sleeve formed on the third linkage $L_3$ to form the third joint $J_3$, and a ball that is pivotally disposed within a socket formed on the first linkage $L_1$ to form the fourth joint $J_4$. While the first and third linkages $L_1$, $L_3$ are representative of first and second adjacent vertebrae, the linkages are also representative of any components that are rigidly coupled to the adjacent vertebrae. Thus, the sleeve of the third linkage $L_3$ can be formed on a connecting element that is rigidly mated to the second vertebra, and the socket of the first linkage $L_1$ can be formed in a connecting element that is rigidly mated to the first vertebra.

Figure 6A:
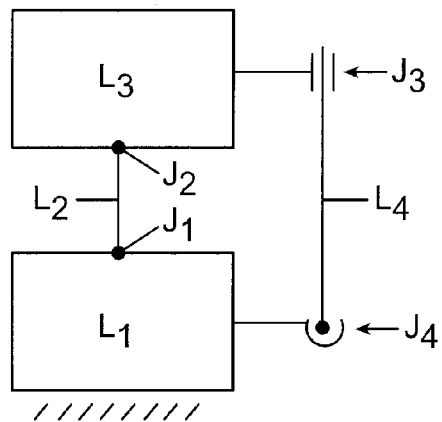
FIG. 6A is a diagram illustrating one embodiment of construct for a spinal stabilization device having a sliding joint and a pivoting joint to kinematically form a four bar linkage mechanism.
Figure 6B:
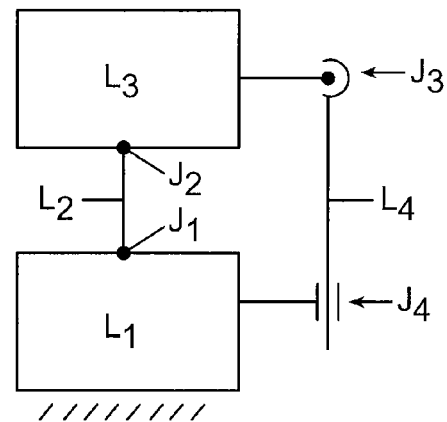
FIG. 6B is a diagram illustrating another embodiment of construct for a spinal stabilization device having a sliding joint and a pivoting joint to kinematically form a four bar linkage mechanism.
Figure 6C:
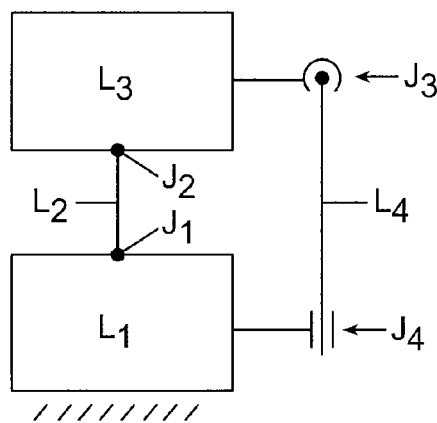
FIG. 6C is a diagram illustrating another embodiment of construct for a spinal stabilization device having a sliding joint and a pivoting joint to kinematically form a four bar linkage mechanism.

FIGS. 6B and 6C illustrate other embodiments of a four bar linkage mechanism that are similar to the four bar linkage mechanism shown in FIG. 6A. However, in the embodiment shown in FIG. 6B the fourth linkage $L_4$ (body) includes a socket formed thereon that rotatably seats a ball formed on the third linkage $L_3$ (second vertebra) to form the third joint $J_3$, and a rod formed thereon that is slidably disposed through a sleeve formed on the first linkage (first vertebra) to form the fourth joint $J_4$. In the embodiment shown in FIG. 6C, the fourth linkage $L_4$ (body) includes a ball formed thereon that is rotatably disposed within a socket formed in the third linkage $L_3$ (second vertebra) to form the third joint $J_3$, and a rod formed thereon that is slidably disposed through a sleeve formed on the first linkage $L_1$ (first vertebra) to form the fourth joint $J_4$.

Figure 6D:
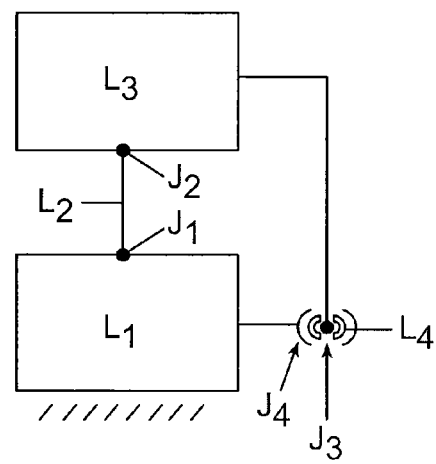
FIG. 6D is a diagram illustrating another embodiment of construct for a spinal stabilization device having a sliding joint and a pivoting joint to kinematically form a four bar linkage mechanism.
Figure 6E:
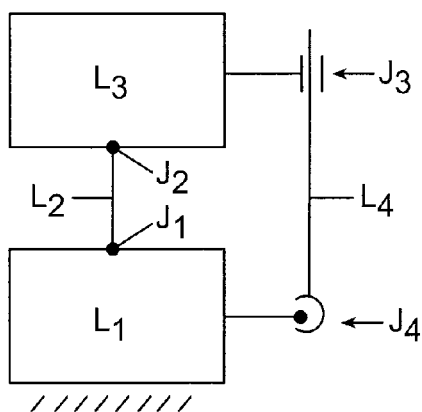
FIG. 6E is a diagram illustrating another embodiment of construct for a spinal stabilization device having a sliding joint and a pivoting joint to kinematically form a four bar linkage mechanism.
Figure 6F:
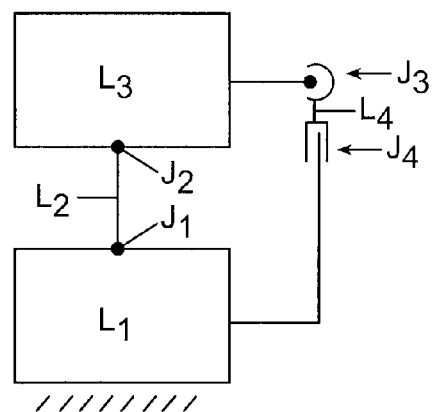
FIG. 6F is a diagram illustrating another embodiment of construct for a spinal stabilization device having a sliding joint and a pivoting joint to kinematically form a four bar linkage mechanism.
Figure 6G:
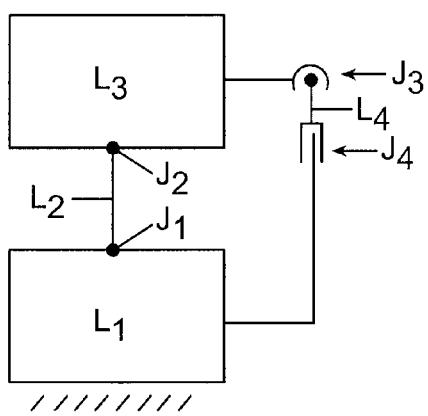
FIG. 6G is a diagram illustrating another embodiment of construct for a spinal stabilization device having a sliding joint and a pivoting joint to kinematically form a four bar linkage mechanism.
Figure 6H:
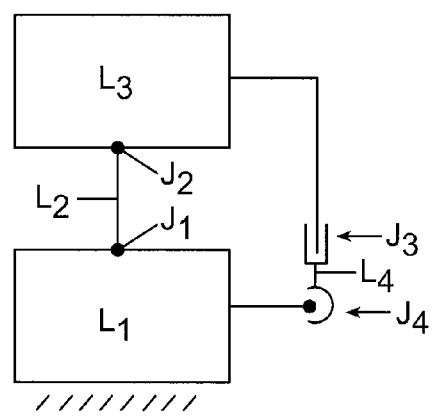
FIG. 6H is a diagram illustrating another embodiment of construct for a spinal stabilization device having a sliding joint and a pivoting joint to kinematically form a four bar linkage mechanism.

FIG. 6D illustrates another possible configuration in which the fourth linkage $L_4$ (body) is in the form of a ball bearing that forms both the third and fourth joints $J_3$, $J_4$. In particular, the ball bearing includes a bore extending therethrough that forms a sleeve for slidably receiving the third linkage $L_3$ (second vertebra) to form the third joint $J_3$, and it is rotatably disposed within a socket formed in the first linkage $L_1$ (first vertebra) to form the fourth joint $J_4$. FIGS. 6E-6H illustrate other various combinations of a fourth linkage $L_4$ having a sliding joint and a pivoting joint.

Figure 7A:
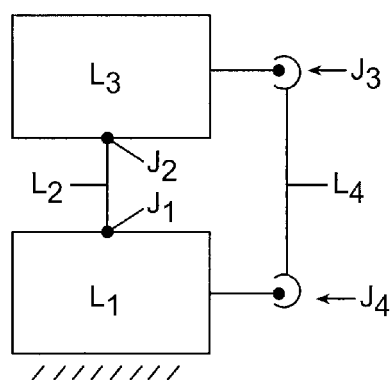
FIG. 7A is a diagram illustrating one embodiment of construct for a spinal stabilization device having two pivoting joints to kinematically form a four bar linkage mechanism.
Figure 7B:
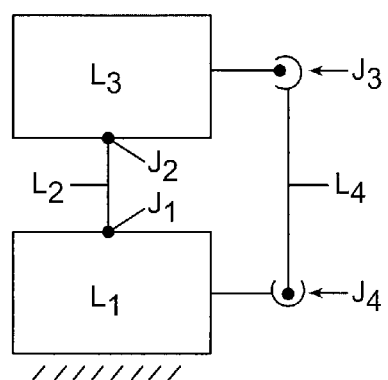
FIG. 7B is a diagram illustrating another embodiment of construct for a spinal stabilization device having two pivoting joints to kinematically form a four bar linkage mechanism.
Figure 7C:
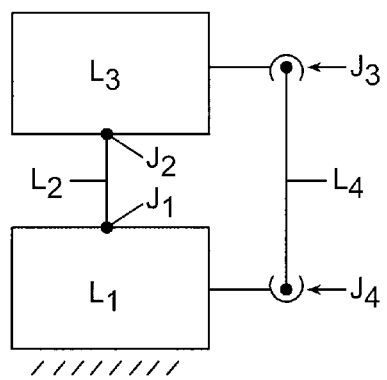
FIG. 7C is a diagram illustrating another embodiment of construct for a spinal stabilization device having two pivoting joints to kinematically form a four bar linkage mechanism.
Figure 7D:
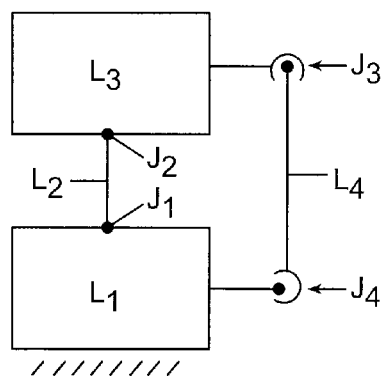
FIG. 7D is a diagram illustrating another embodiment of construct for a spinal stabilization device having two pivoting joints to kinematically form a four bar linkage mechanism.

FIGS. 7A-7D likewise illustrate various combinations for forming a four-bar linkage mechanism, however in these embodiments the third and fourth joints $J_3$, $J_4$ that couple the fourth linkage $L_4$ to the third and first linkages $L_3$, $L_1$ are pivoting joints, e.g., ball and socket joints. In FIG. 7A, the fourth linkage $L_4$ (body) includes a first socket formed therein for receiving a ball formed on the third linkage $L_3$ (second vertebra) to form the third joint $J_3$, and a second socket formed thereon for receiving a ball formed on the fourth linkage $L_4$ (first vertebra) to form the fourth joint $J_4$. In FIG. 7B, the fourth linkage $L_4$ (body) includes a first socket formed therein for receiving a ball formed on the third linkage $L_3$ (second vertebra) to form the third joint $J_3$, and a ball formed thereof that is rotatably disposed within a socket formed on the fourth linkage $L_4$ (first vertebra) to form the fourth joint $J_4$. FIGS. 7C and 7D likewise illustrate various other combinations for forming two ball and socket joints to couple the fourth linkage $L_4$ to the third and first linkages $L_3$, $L_1$. A person skilled in the art will appreciate that FIGS. 6A-7D merely illustrate some possible combinations for coupling a fourth linkage $L_4$ (body) of a four bar linkage mechanism to the third and first linkages $L_3$, $L_1$, and that a variety of other configurations are possible and can be used to construct a spinal stabilization device that kinematically forms a four bar linkage mechanism in the sagittal plane with adjacent vertebrae and a disc disposed therebetween.

A person skilled in the art will appreciate that, while the sliding joints and pivoting joints shown in FIGS. 6A-6H and 7A-7D each represent one translational or rotational degree-of-freedom, that multiple pieces may be used to construct each joint. For example, a sliding joint can be composed of two simple mating surfaces, such as a sleeve and a rod, or it can be composed of multiple pieces, such as a linear ball bearing having multiple balls housed in a casing, to accommodate a sliding motion. A pivoting joint can also be composed of two simple mating surfaces, such as a ball and socket, or it can be composed of multiple pieces, such as a hinge joint with a cylindrical rod.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A system for stabilizing adjacent vertebrae, comprising:
    an artificial disc adapted to be implanted between adjacent vertebrae and having at least one degree of freedom;
    first and second rigid connecting elements;
    first and second anchors adapted to rigidly couple the first and second connecting elements to adjacent vertebrae;
    a rigid body coupled between the first and second connecting elements; and
    a first joint formed between the rigid body and the first connecting element and a second joint formed between the rigid body and the second connecting element such that the first and second connecting elements and the rigid body kinematically form a four bar linkage mechanism in a sagittal plane with the first and second adjacent vertebrae and the artificial disc when the artificial disc is disposed between the first and second adjacent vertebrae for restoring function to the first and second adjacent vertebrae, the first and second joints each having one degree of freedom in the sagittal plane, and at least one of the first and second joints being a sliding joint.

2. The system of claim 1, wherein the first joint is a sliding joint and the second joint is a rotating joint, the sliding joint and the rotating joint together being adapted to allow flexion and extension of first and second adjacent vertebrae.

3. The system of claim 2, wherein the sliding joint is adapted to slide along a curved path in the sagittal plane.

4. The system of claim 2, wherein the sliding joint comprises a sleeve adapted to slidably receive a rod.

5. The system of claim 2, wherein the rotating joint comprises a ball adapted to be rotatably disposed within a socket.

6. The system of claim 2, wherein the rotating joint is a hinge joint.

7. The system of claim 1, wherein the first and second joints each comprise sliding joints that are adapted to allow flexion and extension of first and second adjacent vertebrae.

8. The system of claim 7, wherein the sliding joints each comprise a sleeve that is adapted to slidably receive a rod.

9. The system of claim 1, wherein a center of rotation of each of the first and second joints is positioned substantially horizontal relative to one another.

10. The system of claim 1, wherein at least one of the first and second joints is adapted to slide vertically when the first and second joints are coupled to adjacent vertebrae.

11. A system for stabilizing adjacent vertebrae, comprising:
    an artificial disc adapted to be implanted between adjacent vertebrae and having at least one degree of freedom;
    first and second rigid connecting elements;
    first and second anchors adapted to rigidly couple the first and second connecting elements to adjacent vertebrae;
    a rigid body coupled between the first and second connecting elements; and
    a first joint formed between the rigid body and the first connecting element and a second joint formed between the rigid body and the second connecting element, the first and second joints each being adapted to provide one degree of freedom in a sagittal plane when coupled to adjacent vertebrae such that the rigid body is adapted to restore function to adjacent vertebrae coupled thereto in combination with the artificial disc when the disc is disposed between the adjacent vertebrae, and at least one of the first and second joints being a sliding joint.

12. The system of claim 11, wherein a center of rotation of each of the first and second joints is positioned substantially horizontal relative to one another.

13. The system of claim 11, wherein at least one of the first and second joints is adapted to slide vertically when the first and second joints are coupled to adjacent vertebrae.

14. A system for stabilizing adjacent vertebrae in a patient's spine, comprising:
   an artificial disc adapted to be implanted between adjacent vertebrae and having at least one degree of freedom; and
   an implant having
      first and second rigid linkages,
      first and second anchors adapted to rigidly couple the first and second rigid linkages to first and second adjacent vertebra, and
      a rigid body having a first joint for movably coupling to the first linkage, and a second joint for movably coupling to the second linkage, the first and second joints each having one degree of freedom in a sagittal plane when implanted, and at least one of the first and second joints being a sliding joint;
   wherein, when the artificial disc is implanted between adjacent first and second vertebrae, the first linkage is coupled to the first vertebrae, and the second linkage is coupled to the second vertebrae, the implant and the artificial disc are adapted to kinematically form a four bar linkage mechanism in a sagittal plane to restore function to the first and second adjacent vertebrae.

15. The system of claim 14, wherein the first and second joints are each adapted to slidably move relative to the first and second linkages.

16. The system of claim 15, wherein the first and second joints each comprise a sleeve that is adapted to slidably receive a rod formed on the first and second linkages.

17. The system of claim 14, wherein the first joint is adapted to slidably move relative to the first linkage, and the second joint is adapted to rotatably move relative to the second linkage.

18. The system of claim 17, wherein the first joint comprises a sleeve that is adapted to slidably receive a rod formed on the first linkage, and the second joint comprises a ball that is adapted to be rotatably disposed within a socket formed in the second linkage.

19. The system of claim 18, wherein the sleeve comprises a lumen formed in the ball.

* * * * *